(12) United States Patent
Thacker

(10) Patent No.: US 9,687,649 B2
(45) Date of Patent: *Jun. 27, 2017

(54) NEUROLOGICAL STIMULATION LEAD ANCHORS AND ASSOCIATED SYSTEMS AND METHODS

(71) Applicant: Nevro Corporation, Redwood City, CA (US)

(72) Inventor: James R. Thacker, Homer, AK (US)

(73) Assignee: Nevro Corp., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/016,183

(22) Filed: Feb. 4, 2016

(65) Prior Publication Data

US 2016/0220809 A1 Aug. 4, 2016

Related U.S. Application Data

(63) Continuation of application No. 14/309,830, filed on Jun. 19, 2014, now Pat. No. 9,265,935.

(60) Provisional application No. 61/840,982, filed on Jun. 28, 2013.

(51) Int. Cl.
*A61N 1/00* (2006.01)
*A61N 1/05* (2006.01)

(52) U.S. Cl.
CPC .................... *A61N 1/0558* (2013.01)

(58) Field of Classification Search
CPC .................................................. A61N 1/0558
See application file for complete search history.

(56) References Cited

U.S. PATENT DOCUMENTS

| | | | |
|---|---|---|---|
| 3,867,950 | A | 2/1975 | Fischell |
| 3,982,060 | A | 9/1976 | Avery et al. |
| 4,044,774 | A | 8/1977 | Corbin et al. |
| 4,136,703 | A | 1/1979 | Wittkampf |
| 4,141,365 | A | 2/1979 | Fischell et al. |
| 4,285,347 | A | 8/1981 | Hess |
| 4,328,813 | A | 5/1982 | Ray |
| 4,374,527 | A | 2/1983 | Iversen |
| 4,414,986 | A | 11/1983 | Dickhudt et al. |
| 4,432,377 | A | 2/1984 | Dickhudt |

(Continued)

FOREIGN PATENT DOCUMENTS

| | | |
|---|---|---|
| CN | 101920065 A | 12/2010 |
| EP | 0158316 A2 | 10/1985 |

(Continued)

OTHER PUBLICATIONS

Kulkarni et al., "A two-layered forward model of tissue for electrical impedance tomography," Physiol Meas., 30(6); pp. 1-24, Jun. 2009.

(Continued)

*Primary Examiner* — Scott Getzow
(74) *Attorney, Agent, or Firm* — Perkins Coie LLP

(57) ABSTRACT

A spinal cord lead anchor comprising a longitudinally extending sleeve having an aperture sized and positioned to receive a spinal cord lead. A retainer is disposed around the sleeve and is operative to compress at least a portion of the sleeve against a spinal cord lead extending through the sleeve. A cover extends around the retainer and includes at least one opening formed through the cover to facilitate engaging the retainer with a tool.

6 Claims, 10 Drawing Sheets

(56) References Cited

U.S. PATENT DOCUMENTS

| | | |
|---|---|---|
| 4,462,401 A | 7/1984 | Burgio |
| 4,462,402 A | 7/1984 | Burgio et al. |
| 4,465,079 A | 8/1984 | Dickhudt |
| 4,498,482 A | 2/1985 | Williams |
| 4,519,403 A | 5/1985 | Dickhudt |
| 4,573,448 A | 3/1986 | Kambin |
| 4,579,120 A | 4/1986 | MacGregor |
| 4,585,005 A | 4/1986 | Lue et al. |
| 4,590,942 A | 5/1986 | Brenman et al. |
| 4,590,949 A | 5/1986 | Pohndorf |
| 4,633,889 A | 1/1987 | Talalla et al. |
| 4,658,835 A | 4/1987 | Pohndorf |
| 4,683,895 A * | 8/1987 | Pohndorf ............ A61B 17/0644 248/505 |
| 4,764,132 A | 8/1988 | Stutz, Jr. |
| 4,782,837 A | 11/1988 | Hogan |
| 4,796,642 A | 1/1989 | Harris |
| 4,884,579 A | 12/1989 | Engelson |
| 4,907,602 A | 3/1990 | Sanders |
| 4,919,653 A | 4/1990 | Martinez et al. |
| 4,979,511 A | 12/1990 | Terry, Jr. |
| 4,994,069 A | 2/1991 | Ritchart et al. |
| 5,000,194 A | 3/1991 | van den Honert et al. |
| 5,016,647 A | 5/1991 | Sanders |
| 5,036,862 A | 8/1991 | Pohndorf |
| 5,072,458 A | 12/1991 | Suzuki |
| 5,167,229 A | 12/1992 | Peckham et al. |
| 5,179,962 A | 1/1993 | Dutcher et al. |
| 5,211,165 A | 5/1993 | Dumoulin et al. |
| 5,215,086 A | 6/1993 | Terry, Jr. et al. |
| 5,217,484 A | 6/1993 | Marks |
| 5,231,988 A | 8/1993 | Wernicke et al. |
| 5,263,480 A | 11/1993 | Wernicke et al. |
| 5,269,303 A | 12/1993 | Wernicke et al. |
| 5,273,053 A | 12/1993 | Pohndorf |
| 5,299,569 A | 4/1994 | Wernicke et al. |
| 5,312,356 A | 5/1994 | Engelson et al. |
| 5,325,873 A | 7/1994 | Hirschi et al. |
| 5,344,438 A | 9/1994 | Testerman et al. |
| 5,351,687 A | 10/1994 | Kroll et al. |
| 5,360,441 A | 11/1994 | Otten |
| 5,417,719 A | 5/1995 | Hull |
| 5,425,367 A | 6/1995 | Shapiro et al. |
| 5,464,446 A | 11/1995 | Dreessen et al. |
| 5,476,494 A | 12/1995 | Edell et al. |
| 5,480,421 A | 1/1996 | Otten |
| 5,484,445 A | 1/1996 | Knuth et al. |
| 5,527,338 A | 6/1996 | Purdy |
| 5,531,778 A | 7/1996 | Maschino et al. |
| 5,571,150 A | 11/1996 | Wernicke et al. |
| 5,669,882 A | 9/1997 | Pyles |
| 5,693,067 A | 12/1997 | Purdy |
| 5,728,148 A | 3/1998 | Bostrom et al. |
| 5,733,322 A | 3/1998 | Starkebaum |
| 5,776,171 A | 7/1998 | Peckham et al. |
| 5,782,898 A | 7/1998 | Dahl et al. |
| 5,824,030 A | 10/1998 | Yang et al. |
| 5,843,146 A | 12/1998 | Cross, Jr. |
| 5,843,148 A | 12/1998 | Gijsbers |
| 5,846,226 A | 12/1998 | Urmey |
| 5,848,126 A | 12/1998 | Fujita et al. |
| 5,865,843 A | 2/1999 | Baudino |
| 5,871,487 A | 2/1999 | Warner et al. |
| 5,871,531 A | 2/1999 | Struble |
| 5,895,416 A | 4/1999 | Barreras |
| 5,925,062 A | 7/1999 | Purdy |
| 5,927,277 A | 7/1999 | Baudino et al. |
| 5,954,758 A | 9/1999 | Peckham et al. |
| 5,957,912 A | 9/1999 | Heitzmann |
| 5,957,965 A | 9/1999 | Moumane et al. |
| 6,026,328 A | 2/2000 | Peckham et al. |
| 6,044,304 A | 3/2000 | Baudino |
| 6,055,456 A | 4/2000 | Gerber |
| 6,066,165 A | 5/2000 | Racz |
| 6,104,956 A | 8/2000 | Naritoku |
| 6,104,960 A | 8/2000 | Duysens |
| 6,106,460 A | 8/2000 | Panescu et al. |
| 6,134,477 A | 10/2000 | Knuteson |
| 6,159,163 A | 12/2000 | Strauss et al. |
| 6,161,047 A | 12/2000 | King et al. |
| 6,175,769 B1 | 1/2001 | Errico et al. |
| 6,192,279 B1 | 2/2001 | Barreras, Sr. et al. |
| 6,198,963 B1 | 3/2001 | Haim et al. |
| 6,205,359 B1 | 3/2001 | Boveja |
| 6,210,417 B1 | 4/2001 | Baudino et al. |
| 6,233,488 B1 | 5/2001 | Hess |
| 6,248,080 B1 | 6/2001 | Miesel et al. |
| 6,248,112 B1 | 6/2001 | Gambale et al. |
| 6,263,230 B1 | 7/2001 | Haynor et al. |
| 6,269,270 B1 | 7/2001 | Boveja |
| 6,292,695 B1 | 9/2001 | Webster, Jr. et al. |
| 6,292,702 B1 | 9/2001 | King et al. |
| 6,304,785 B1 | 10/2001 | McCreery et al. |
| 6,319,241 B1 | 11/2001 | King et al. |
| 6,321,104 B1 | 11/2001 | Gielen et al. |
| 6,325,778 B1 | 12/2001 | Zadno-Azizi et al. |
| 6,339,725 B1 | 1/2002 | Naritoku et al. |
| 6,356,788 B2 | 3/2002 | Boveja |
| 6,360,750 B1 | 3/2002 | Gerber et al. |
| 6,464,668 B1 | 10/2002 | Pace |
| 6,549,812 B1 | 4/2003 | Smits |
| 6,600,956 B2 | 7/2003 | Maschino et al. |
| 6,601,585 B1 | 8/2003 | Conrad et al. |
| 6,615,085 B1 | 9/2003 | Boveja |
| 6,626,181 B1 | 9/2003 | Knudson et al. |
| 6,634,362 B2 | 10/2003 | Conrad et al. |
| 6,699,243 B2 | 3/2004 | West et al. |
| 6,725,096 B2 | 4/2004 | Chinn et al. |
| 6,733,500 B2 | 5/2004 | Kelley et al. |
| 6,836,687 B2 | 12/2004 | Kelley et al. |
| 6,875,571 B2 | 4/2005 | Crabtree et al. |
| 6,920,359 B2 | 7/2005 | Meadows et al. |
| 6,934,589 B2 | 8/2005 | Sundquist et al. |
| 6,937,896 B1 | 8/2005 | Kroll |
| RE38,972 E | 2/2006 | Purdy |
| 7,069,083 B2 | 6/2006 | Finch et al. |
| 7,072,719 B2 | 7/2006 | Vinup et al. |
| 7,076,305 B2 | 7/2006 | Imran et al. |
| 7,089,057 B2 | 8/2006 | Heathershaw et al. |
| 7,090,661 B2 | 8/2006 | Morris et al. |
| 7,107,097 B2 | 9/2006 | Stern et al. |
| 7,107,100 B2 | 9/2006 | Imran et al. |
| 7,107,104 B2 | 9/2006 | Keravel et al. |
| 7,120,498 B2 | 10/2006 | Imran et al. |
| 7,146,224 B2 | 12/2006 | King |
| 7,160,258 B2 | 1/2007 | Imran et al. |
| 7,164,944 B1 | 1/2007 | Kroll et al. |
| 7,174,219 B2 | 2/2007 | Wahlstrand et al. |
| 7,177,702 B2 | 2/2007 | Wallace et al. |
| 7,177,703 B2 | 2/2007 | Boveja et al. |
| 7,182,726 B2 | 2/2007 | Williams et al. |
| 7,184,838 B2 | 2/2007 | Cross, Jr. |
| 7,184,840 B2 | 2/2007 | Stolz et al. |
| 7,184,842 B2 | 2/2007 | Seifert et al. |
| 7,187,982 B2 | 3/2007 | Seifert et al. |
| 7,191,018 B2 | 3/2007 | Gielen et al. |
| 7,194,301 B2 | 3/2007 | Jenkins et al. |
| 7,206,642 B2 | 4/2007 | Pardo et al. |
| 7,209,787 B2 | 4/2007 | DiLorenzo |
| 7,212,867 B2 | 5/2007 | Van Venrooij et al. |
| 7,270,650 B2 | 9/2007 | Morris et al. |
| 7,277,758 B2 | 10/2007 | DiLorenzo |
| 7,328,068 B2 | 2/2008 | Spinelli et al. |
| 7,328,069 B2 | 2/2008 | Gerber |
| 7,330,762 B2 | 2/2008 | Boveja et al. |
| 7,337,005 B2 | 2/2008 | Kim et al. |
| 7,337,006 B2 | 2/2008 | Kim et al. |
| 7,363,089 B2 | 4/2008 | Vinup et al. |
| 7,369,894 B2 | 5/2008 | Gerber |
| 7,379,776 B1 | 5/2008 | Chitre et al. |
| 7,383,090 B2 | 6/2008 | O'Brien et al. |
| 7,384,390 B2 | 6/2008 | Furness et al. |
| 7,386,341 B2 | 6/2008 | Hafer et al. |
| 7,393,351 B2 | 7/2008 | Woloszko et al. |

(56) References Cited

U.S. PATENT DOCUMENTS

| | | |
|---|---|---|
| 7,418,292 B2 | 8/2008 | Shafer |
| 7,421,297 B2 | 9/2008 | Giftakis et al. |
| 7,447,546 B2 | 11/2008 | Kim et al. |
| 7,450,993 B2 | 11/2008 | Kim et al. |
| 7,455,666 B2 | 11/2008 | Purdy |
| 7,460,913 B2 | 12/2008 | Kuzma et al. |
| 7,483,754 B2 | 1/2009 | Imran et al. |
| 7,502,651 B2 | 3/2009 | Kim et al. |
| 7,546,164 B2 | 6/2009 | King |
| 7,547,317 B2 | 6/2009 | Cragg |
| 7,553,307 B2 | 6/2009 | Bleich et al. |
| 7,582,053 B2 | 9/2009 | Gross et al. |
| 7,590,454 B2 | 9/2009 | Garabedian et al. |
| 7,604,644 B2 | 10/2009 | Schulte et al. |
| 7,613,516 B2 | 11/2009 | Cohen et al. |
| 7,684,873 B2 | 3/2010 | Gerber |
| 7,697,972 B2 | 4/2010 | Verard et al. |
| 7,697,995 B2 | 4/2010 | Cross, Jr. et al. |
| 7,702,386 B2 | 4/2010 | Dobak et al. |
| 7,715,924 B2 | 5/2010 | Rezai et al. |
| 7,717,938 B2 | 5/2010 | Kim et al. |
| 7,738,968 B2 | 6/2010 | Bleich |
| 7,742,818 B2 | 6/2010 | Dinsmoor et al. |
| 7,769,442 B2 | 8/2010 | Shafer |
| 7,780,679 B2 | 8/2010 | Bobo, Sr. et al. |
| 7,781,215 B2 | 8/2010 | Ingham et al. |
| 7,797,057 B2 | 9/2010 | Harris |
| 7,810,233 B2 | 10/2010 | Krulevitch et al. |
| 7,810,996 B1 | 10/2010 | Giphart et al. |
| 7,822,482 B2 | 10/2010 | Gerber |
| 7,829,694 B2 | 11/2010 | Kaemmerer |
| 7,854,763 B2 | 12/2010 | Andrieu et al. |
| 7,857,857 B2 | 12/2010 | Kim |
| 7,860,568 B2 | 12/2010 | Deininger et al. |
| 7,881,806 B2 | 2/2011 | Horrigan et al. |
| 7,904,149 B2 | 3/2011 | Gerber |
| 7,918,849 B2 | 4/2011 | Bleich et al. |
| 7,937,144 B2 | 5/2011 | Dobak |
| 7,967,839 B2 | 6/2011 | Flock et al. |
| 7,987,000 B2 | 7/2011 | Moffitt et al. |
| 7,996,055 B2 | 8/2011 | Hauck et al. |
| 7,998,175 B2 | 8/2011 | Kim |
| 8,000,805 B2 | 8/2011 | Swoyer et al. |
| 8,010,207 B2 | 8/2011 | Smits et al. |
| 8,019,422 B2 | 9/2011 | Imran et al. |
| 8,024,035 B2 | 9/2011 | Dobak, III |
| 8,036,756 B2 | 10/2011 | Swoyer et al. |
| 8,075,595 B2 | 12/2011 | Kim |
| 8,078,280 B2 | 12/2011 | Sage |
| 8,099,172 B2 | 1/2012 | Swanson |
| 8,123,807 B2 | 2/2012 | Kim |
| 8,494,652 B2 | 7/2013 | Cantlon et al. |
| 8,731,671 B2 | 5/2014 | Rodby et al. |
| 9,265,935 B2 | 2/2016 | Thacker et al. |
| 2001/0014820 A1 | 8/2001 | Gielen et al. |
| 2001/0016765 A1 | 8/2001 | Gielen et al. |
| 2001/0025192 A1 | 9/2001 | Gerber et al. |
| 2001/0027336 A1 | 10/2001 | Gielen et al. |
| 2002/0022872 A1 | 2/2002 | Gielen et al. |
| 2002/0042642 A1 | 4/2002 | Gerber |
| 2002/0052640 A1 | 5/2002 | Bigus et al. |
| 2002/0087151 A1 | 7/2002 | Mody et al. |
| 2002/0111658 A1 | 8/2002 | Greenberg et al. |
| 2002/0128700 A1 | 9/2002 | Cross |
| 2002/0173718 A1 | 11/2002 | Frisch et al. |
| 2003/0055476 A1 | 3/2003 | Vinup et al. |
| 2003/0078633 A1 | 4/2003 | Firlik et al. |
| 2003/0097166 A1 | 5/2003 | Krulevitch et al. |
| 2003/0114752 A1 | 6/2003 | Henderson et al. |
| 2003/0114895 A1 | 6/2003 | Gordon et al. |
| 2003/0125786 A1 | 7/2003 | Gliner et al. |
| 2003/0136418 A1 | 7/2003 | Behm |
| 2003/0199949 A1 | 10/2003 | Pardo |
| 2003/0199951 A1 | 10/2003 | Pardo et al. |
| 2003/0199952 A1 | 10/2003 | Stolz et al. |
| 2003/0199953 A1 | 10/2003 | Stolz et al. |
| 2003/0199962 A1 | 10/2003 | Struble et al. |
| 2003/0204228 A1 | 10/2003 | Cross et al. |
| 2003/0208247 A1 | 11/2003 | Spinelli et al. |
| 2003/0220677 A1 | 11/2003 | Doan et al. |
| 2004/0024440 A1 | 2/2004 | Cole |
| 2004/0049240 A1 | 3/2004 | Gerber et al. |
| 2004/0087877 A1 | 5/2004 | Besz et al. |
| 2004/0088033 A1 | 5/2004 | Smits et al. |
| 2004/0088034 A1 | 5/2004 | Smits et al. |
| 2004/0093051 A1 | 5/2004 | Chinn et al. |
| 2004/0093053 A1 | 5/2004 | Gerber et al. |
| 2004/0097803 A1 | 5/2004 | Panescu |
| 2004/0147976 A1 | 7/2004 | Gordon et al. |
| 2004/0162601 A1 | 8/2004 | Smits |
| 2004/0186543 A1 | 9/2004 | King et al. |
| 2004/0186544 A1 | 9/2004 | King |
| 2004/0193228 A1 | 9/2004 | Gerber |
| 2004/0215301 A1 | 10/2004 | Lokhoff et al. |
| 2004/0215307 A1 | 10/2004 | Michels et al. |
| 2004/0236387 A1 | 11/2004 | Fang et al. |
| 2004/0243101 A1 | 12/2004 | Gillis |
| 2004/0243206 A1 | 12/2004 | Tadlock |
| 2005/0004417 A1 | 1/2005 | Nelson et al. |
| 2005/0004638 A1 | 1/2005 | Cross |
| 2005/0010260 A1 | 1/2005 | Gerber |
| 2005/0015128 A1 | 1/2005 | Rezai et al. |
| 2005/0020970 A1 | 1/2005 | Gerber |
| 2005/0021092 A1 | 1/2005 | Yun et al. |
| 2005/0027338 A1 | 2/2005 | Hill |
| 2005/0033372 A1 | 2/2005 | Gerber |
| 2005/0033373 A1 | 2/2005 | Gerber |
| 2005/0033374 A1 | 2/2005 | Gerber |
| 2005/0049648 A1 | 3/2005 | Cohen et al. |
| 2005/0049664 A1 | 3/2005 | Harris et al. |
| 2005/0055064 A1 | 3/2005 | Meadows et al. |
| 2005/0065588 A1 | 3/2005 | Zhao et al. |
| 2005/0070969 A1 | 3/2005 | Gerber |
| 2005/0070974 A1 | 3/2005 | Knudson et al. |
| 2005/0075684 A1 | 4/2005 | Phillips et al. |
| 2005/0075702 A1 | 4/2005 | Shafer |
| 2005/0075707 A1 | 4/2005 | Meadows et al. |
| 2005/0090885 A1 | 4/2005 | Harris et al. |
| 2005/0096750 A1 | 5/2005 | Kagan et al. |
| 2005/0101977 A1 | 5/2005 | Gannoe et al. |
| 2005/0113878 A1 | 5/2005 | Gerber |
| 2005/0131506 A1 | 6/2005 | Rezai et al. |
| 2005/0137644 A1 | 6/2005 | Boveja et al. |
| 2005/0148951 A1 | 7/2005 | Gonon |
| 2005/0149157 A1 | 7/2005 | Hunter et al. |
| 2005/0165465 A1 | 7/2005 | Pianca et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182420 A1 | 8/2005 | Schulte et al. |
| 2005/0182421 A1 | 8/2005 | Schulte et al. |
| 2005/0182422 A1 | 8/2005 | Schulte et al. |
| 2005/0182424 A1 | 8/2005 | Schulte et al. |
| 2005/0182425 A1 | 8/2005 | Schulte et al. |
| 2005/0182455 A1 | 8/2005 | Thrope et al. |
| 2005/0182463 A1 | 8/2005 | Hunter et al. |
| 2005/0182467 A1 | 8/2005 | Hunter et al. |
| 2005/0182468 A1 | 8/2005 | Hunter et al. |
| 2005/0182469 A1 | 8/2005 | Hunter et al. |
| 2005/0183731 A1 | 8/2005 | Hunter et al. |
| 2005/0187600 A1 | 8/2005 | Hunter et al. |
| 2005/0192647 A1 | 9/2005 | Hunter et al. |
| 2005/0196421 A1 | 9/2005 | Hunter et al. |
| 2005/0203599 A1 | 9/2005 | Garabedian et al. |
| 2005/0203600 A1 | 9/2005 | Wallace et al. |
| 2005/0209665 A1 | 9/2005 | Hunter et al. |
| 2005/0209667 A1 | 9/2005 | Erickson et al. |
| 2005/0215942 A1 | 9/2005 | Abrahamson et al. |
| 2005/0222642 A1 | 10/2005 | Przybyszewski et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0228221 A1 | 10/2005 | Hirakawa |

(56) References Cited

U.S. PATENT DOCUMENTS

| | | |
|---|---|---|
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0251237 A1 | 11/2005 | Kuzma et al. |
| 2005/0283053 A1 | 12/2005 | deCharms |
| 2006/0004429 A1 | 1/2006 | Mrva et al. |
| 2006/0041277 A1 | 2/2006 | Deem et al. |
| 2006/0041295 A1 | 2/2006 | Osypka |
| 2006/0052765 A1 | 3/2006 | Pyles et al. |
| 2006/0052836 A1 | 3/2006 | Kim et al. |
| 2006/0084982 A1 | 4/2006 | Kim |
| 2006/0084983 A1 | 4/2006 | Kim |
| 2006/0085069 A1 | 4/2006 | Kim |
| 2006/0085070 A1 | 4/2006 | Kim |
| 2006/0089691 A1 | 4/2006 | Kaplan et al. |
| 2006/0089692 A1 | 4/2006 | Cross et al. |
| 2006/0089695 A1 | 4/2006 | Bolea et al. |
| 2006/0089696 A1 | 4/2006 | Olsen et al. |
| 2006/0089697 A1 | 4/2006 | Cross et al. |
| 2006/0095134 A1 | 5/2006 | Trieu et al. |
| 2006/0122620 A1 | 6/2006 | Kim |
| 2006/0122678 A1 | 6/2006 | Olsen et al. |
| 2006/0161235 A1 | 7/2006 | King |
| 2006/0161236 A1 | 7/2006 | King |
| 2006/0167525 A1 | 7/2006 | King |
| 2006/0168805 A1 | 8/2006 | Hegland et al. |
| 2006/0173262 A1 | 8/2006 | Hegland et al. |
| 2006/0206118 A1 | 9/2006 | Kim et al. |
| 2006/0224102 A1 | 10/2006 | Glenn |
| 2006/0247747 A1 | 11/2006 | Olsen et al. |
| 2006/0247748 A1 | 11/2006 | Wahlstrand et al. |
| 2006/0247776 A1 | 11/2006 | Kim |
| 2006/0253182 A1 | 11/2006 | King |
| 2006/0259110 A1 | 11/2006 | Wallace et al. |
| 2006/0264122 A1 | 11/2006 | Aman et al. |
| 2006/0265039 A1 | 11/2006 | Bartic et al. |
| 2007/0005140 A1 | 1/2007 | Kim et al. |
| 2007/0021786 A1 | 1/2007 | Parnis et al. |
| 2007/0027486 A1 | 2/2007 | Armstrong |
| 2007/0027514 A1 | 2/2007 | Gerber |
| 2007/0027515 A1 | 2/2007 | Gerber |
| 2007/0032836 A1 | 2/2007 | Thrope et al. |
| 2007/0050004 A1 | 3/2007 | Swoyer et al. |
| 2007/0050005 A1 | 3/2007 | Lauro |
| 2007/0055332 A1 | 3/2007 | Swoyer |
| 2007/0060973 A1 | 3/2007 | Ludvig et al. |
| 2007/0073355 A1 | 3/2007 | Dilorenzo |
| 2007/0088414 A1 | 4/2007 | Campbell et al. |
| 2007/0100408 A1 | 5/2007 | Gerber |
| 2007/0106289 A1 | 5/2007 | O'Sullivan |
| 2007/0112404 A1 | 5/2007 | Mann et al. |
| 2007/0123888 A1 | 5/2007 | Bleich et al. |
| 2007/0135881 A1 | 6/2007 | Vilims |
| 2007/0150036 A1 | 6/2007 | Anderson |
| 2007/0161919 A1 | 7/2007 | DiLorenzo |
| 2007/0162085 A1 | 7/2007 | DiLorenzo |
| 2007/0168008 A1 | 7/2007 | Olsen |
| 2007/0179580 A1 | 8/2007 | Colborn |
| 2007/0191903 A1 | 8/2007 | Bruinstroop |
| 2007/0191904 A1 | 8/2007 | Libbus et al. |
| 2007/0198063 A1 | 8/2007 | Hunter et al. |
| 2007/0203540 A1 | 8/2007 | Goetz et al. |
| 2007/0213795 A1 | 9/2007 | Bradley et al. |
| 2007/0244520 A1 | 10/2007 | Ferren et al. |
| 2007/0255340 A1 | 11/2007 | Giftakis et al. |
| 2007/0255341 A1 | 11/2007 | Giftakis et al. |
| 2007/0255364 A1 | 11/2007 | Gerber et al. |
| 2007/0255365 A1 | 11/2007 | Gerber et al. |
| 2007/0255366 A1 | 11/2007 | Gerber et al. |
| 2007/0255367 A1 | 11/2007 | Gerber et al. |
| 2007/0255368 A1 | 11/2007 | Bonde et al. |
| 2007/0255369 A1 | 11/2007 | Bonde et al. |
| 2007/0255383 A1 | 11/2007 | Gerber et al. |
| 2007/0261115 A1 | 11/2007 | Gerber et al. |
| 2007/0276450 A1 | 11/2007 | Meadows et al. |
| 2008/0027505 A1 | 1/2008 | Levin et al. |
| 2008/0046036 A1 | 2/2008 | King et al. |
| 2008/0103569 A1 | 5/2008 | Gerber |
| 2008/0103570 A1 | 5/2008 | Gerber |
| 2008/0103572 A1 | 5/2008 | Gerber |
| 2008/0103576 A1 | 5/2008 | Gerber |
| 2008/0103578 A1 | 5/2008 | Gerber |
| 2008/0103579 A1 | 5/2008 | Gerber |
| 2008/0103580 A1 | 5/2008 | Gerber |
| 2008/0140087 A1 | 6/2008 | Barbagli |
| 2008/0140152 A1 | 6/2008 | Imran et al. |
| 2008/0140169 A1 | 6/2008 | Imran |
| 2008/0147156 A1 | 6/2008 | Imran |
| 2008/0177339 A1 | 7/2008 | Bolea et al. |
| 2008/0177364 A1 | 7/2008 | Bolea et al. |
| 2008/0183221 A1 | 7/2008 | Burdulis |
| 2008/0183224 A1 | 7/2008 | Barolat |
| 2008/0183257 A1 | 7/2008 | Imran et al. |
| 2008/0216846 A1 | 9/2008 | Levin |
| 2008/0243218 A1 | 10/2008 | Bottomley et al. |
| 2008/0262430 A1 | 10/2008 | Anderson et al. |
| 2008/0275467 A1 | 11/2008 | Liao et al. |
| 2008/0319311 A1 | 12/2008 | Hamadeh |
| 2009/0018630 A1 | 1/2009 | Osypka et al. |
| 2009/0024075 A1 | 1/2009 | Schroeppel et al. |
| 2009/0099439 A1 | 4/2009 | Barolat |
| 2009/0112272 A1 | 4/2009 | Schleicher et al. |
| 2009/0112301 A1 | 4/2009 | Kowalczyk |
| 2009/0125060 A1 | 5/2009 | Rivard et al. |
| 2009/0204119 A1 | 8/2009 | Bleich et al. |
| 2009/0216306 A1 | 8/2009 | Barker |
| 2009/0270940 A1 | 10/2009 | Deininger et al. |
| 2010/0004654 A1 | 1/2010 | Schmitz et al. |
| 2010/0036454 A1 | 2/2010 | Bennett et al. |
| 2010/0057162 A1 | 3/2010 | Moffitt et al. |
| 2010/0057163 A1 | 3/2010 | Moffitt et al. |
| 2010/0057164 A1 | 3/2010 | Moffitt et al. |
| 2010/0057165 A1 | 3/2010 | Moffitt et al. |
| 2010/0057177 A1 | 3/2010 | Moffitt et al. |
| 2010/0070010 A1 | 3/2010 | Simpson |
| 2010/0094116 A1 | 4/2010 | Silverstein |
| 2010/0094231 A1 | 4/2010 | Bleich et al. |
| 2010/0100158 A1 | 4/2010 | Thrope et al. |
| 2010/0137943 A1 | 6/2010 | Zhu |
| 2010/0137944 A1 | 6/2010 | Zhu |
| 2010/0145221 A1 | 6/2010 | Brunnett et al. |
| 2010/0145427 A1 | 6/2010 | Gliner et al. |
| 2010/0152538 A1 | 6/2010 | Gleason et al. |
| 2010/0179562 A1 | 7/2010 | Linker et al. |
| 2010/0256720 A1 | 10/2010 | Overstreet et al. |
| 2010/0274314 A1 | 10/2010 | Alataris et al. |
| 2010/0274315 A1 | 10/2010 | Alataris et al. |
| 2010/0274326 A1 | 10/2010 | Chitre et al. |
| 2010/0274336 A1 | 10/2010 | Nguyen-Stella et al. |
| 2010/0292769 A1 | 11/2010 | Brounstein et al. |
| 2010/0298905 A1 | 11/2010 | Simon |
| 2010/0312319 A1 | 12/2010 | Barker |
| 2010/0318165 A1 | 12/2010 | Harris |
| 2011/0022114 A1 | 1/2011 | Navarro |
| 2011/0022141 A1 | 1/2011 | Chen et al. |
| 2011/0022142 A1 | 1/2011 | Barker et al. |
| 2011/0022143 A1 | 1/2011 | North |
| 2011/0031961 A1 | 2/2011 | Durand et al. |
| 2011/0046617 A1 | 2/2011 | Thompson et al. |
| 2011/0071540 A1 | 3/2011 | Kast et al. |
| 2011/0071593 A1 | 3/2011 | Parker et al. |
| 2011/0071604 A1 | 3/2011 | Wahlstrand et al. |
| 2011/0106052 A1 | 5/2011 | Chiang et al. |
| 2011/0112609 A1 | 5/2011 | Peterson |
| 2011/0144468 A1 | 6/2011 | Boggs et al. |
| 2011/0224710 A1 | 9/2011 | Bleich |
| 2011/0230943 A1 | 9/2011 | Johnson et al. |
| 2011/0264181 A1 | 10/2011 | Hamilton |
| 2012/0083709 A1 | 4/2012 | Parker et al. |
| 2012/0232626 A1 | 9/2012 | Daglow |
| 2016/0059006 A1 | 3/2016 | Doan et al. |
| 2016/0302827 A1 | 10/2016 | Chitre et al. |

(56) References Cited

U.S. PATENT DOCUMENTS

2016/0354609 A1  12/2016 Parker et al.
2016/0360993 A1  12/2016 Thacker et al.

FOREIGN PATENT DOCUMENTS

| SU | 1648430 A1 | 5/1991 |
|----|------------|--------|
| SU | 1690727 A1 | 11/1991 |
| WO | WO-9003824 A1 | 4/1990 |
| WO | WO-2008094952 A2 | 8/2008 |

OTHER PUBLICATIONS

"Clik Anchor SC-4316," Boston Scientific Corporation, 2011, 1 page.
Intrel® Model 7490 / 7491 Extensions for Spinal Cord Stimulation (SCS), Medtronic Neuro, Minneapolis, MN 1984, 9 pages.
Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
Medtronic, "Physician and Hospital Staff Manual," InterStrim System, Neurological Division. 93 pages, undated.
International Search Report and Written Opinion for International Patent Application No. PCT/US2014/043522, Applicant: Nevro Corporation; mailed Aug. 14, 2014, 6 pages.

* cited by examiner

NEUROLOGICAL STIMULATION LEAD ANCHORS AND ASSOCIATED SYSTEMS AND METHODS

CROSS REFERENCE TO RELATED APPLICATION

The present application is a continuation of U.S. patent application Ser. No. 14/309,830, filed Jun. 19, 2014, which claims priority to U.S. Provisional Application No. 61/840,982, filed Jun. 28, 2013, which are incorporated herein by reference in its entirety.

TECHNICAL FIELD

The present disclosure is directed generally to lead anchors for positioning and securing neurological stimulation system leads or other signal delivery elements. More specifically, the disclosure is directed to lead anchors for positioning and securing spinal cord stimulation and modulation leads.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological or muscle tissue. For example, several neurological stimulation systems have cylindrical leads that include a lead body with a circular cross-sectional shape and one or more conductive rings (i.e., contacts) spaced apart from each other at the distal end of the lead body. The conductive rings operate as individual electrodes and, in many cases, the leads are implanted percutaneously through a large needle inserted into the epidural space, with or without the assistance of a stylet.

Once implanted, the signal generator applies electrical pulses to the electrodes, which in turn modify the function of the patient's nervous system, such as by altering the patient's responsiveness to sensory stimuli and/or altering the patient's motor-circuit output. In pain treatment, the signal generator applies electrical pulses to the electrodes, which in turn can mask or otherwise alter the patient's sensation of pain.

It is important to accurately position and anchor the leads in order to provide effective therapy. For example, in both traditional low frequency spinal cord stimulation (SCS) and high frequency spinal cord modulation therapy, one or more leads are positioned along a patient's spine to provide therapy to a specific vertebral area. Existing lead anchors can negatively impact lead performance and/or reliability when they allow the lead body to slide or otherwise change position relative to a treatment area. The movement of the lead body relative to the lead anchor can reduce the accuracy with which the stimulation is provided, thus limiting the effectiveness of the therapy. In some cases, the leads must be securely fixed but still be repositionable if a practitioner determines that a different position would provide more effective therapy. As a result, there exists a need for a lead retention mechanism, such as a lead anchor, that mitigates lead movement while providing the ability to subsequently reposition the lead.

DETAILED DESCRIPTION

The present technology is directed generally to lead anchors and methods of anchoring a lead to a patient that mitigate lead movement while providing the ability to subsequently reposition the lead. In general, the lead anchors and methods are for use with neurological stimulation systems, such as spinal cord modulation systems. In particular embodiments, the lead anchor can include a retainer, such as a snap ring or circlip that releasably attaches a lead to a lead anchor. The lead anchor can in turn be attached to a patient with sutures. Specific details of several embodiments of the technology are described below with reference to representative anchors to provide a thorough understanding of these embodiments, but other embodiments can have other arrangements. Several details describing structures or processes that are well-known and often associated with lead anchors and associated devices but that may unnecessarily obscure some significant aspects of the disclosure are not set forth in the following description for purposes of clarity. Moreover, although the following disclosure sets forth several embodiments of different aspects of the technology, several other embodiments of the technology can have different configurations or different components than those described in this section. As such, the technology may have other embodiments with additional elements and/or without several of the elements described below with reference to FIGS. 1-9.

Figure 1:
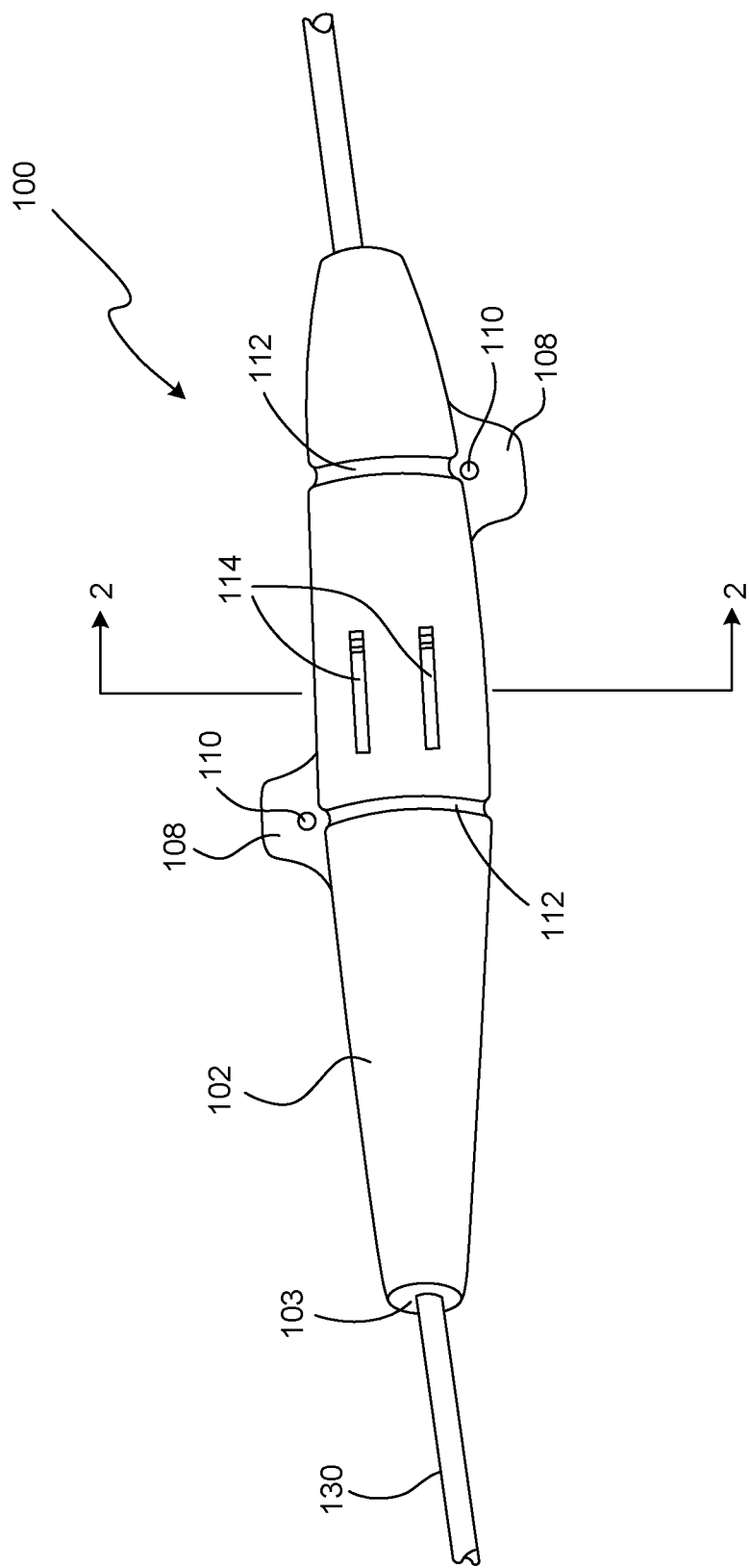
FIG. 1 is a perspective view of a lead anchor according to a representative embodiment.

FIG. 1 illustrates a lead anchor 100 according to a representative embodiment of the present technology. The lead anchor 100 releasably carries a lead 130 (e.g., an electrical stimulation or modulation lead) and anchors the lead 130 relative to a patient's tissue. Accordingly, the lead anchor 100 can include a longitudinally extending anchor body 102 having a longitudinally extending aperture 103 that receives the lead 130. One or more anchor tabs 108 extend laterally from the anchor body 102 e.g., on opposite sides. Each anchor tab 108 can include an aperture 110 or other feature to facilitate attaching the lead anchor 100 to a patient's tissue. The lead anchor 100 can include an associated groove 112 that is aligned with a corresponding aperture 110. The grooves 112 act to keep sutures, which are used to attach the anchor 100 to the patient, properly aligned with the anchor tabs 108 and the apertures 110. Thus, the lead anchor 100 may be attached to a patient by suturing through the apertures 110 with the suture threads captured in the grooves 112. The lead anchor 100 can further include openings 114 that allow a user to attach and release the anchor 100 and the lead 130, as described further with reference to FIG. 3.

Figure 2:
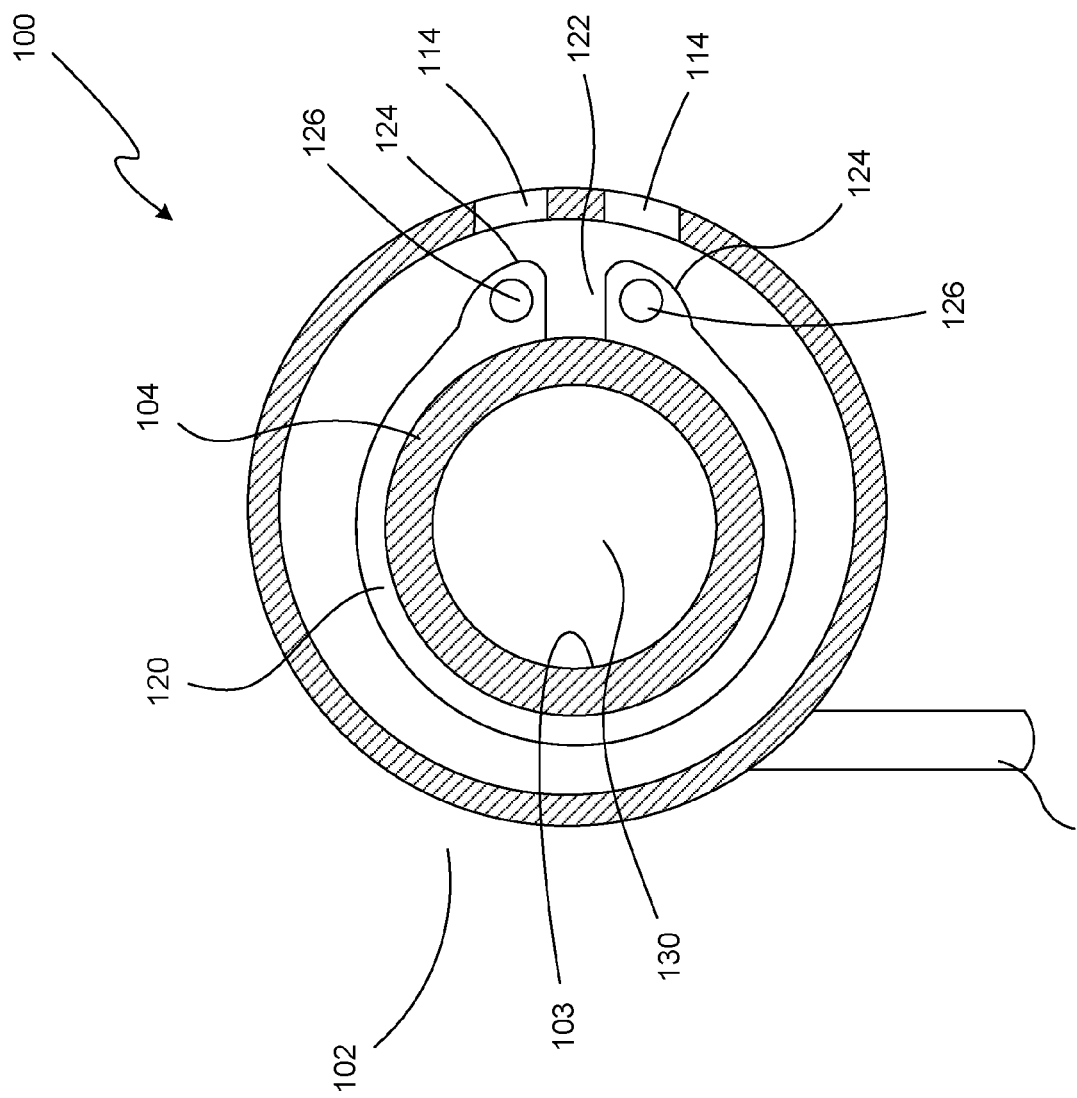
FIG. 2 is a cross sectional view of the lead anchor shown in FIG. 1 taken along line 2-2 of FIG. 1.

FIG. 2 illustrates a cross-sectional view of an embodiment of the anchor 100 shown in FIG. 1. The anchor body 102 includes a sleeve 104 in which the longitudinally extending aperture 103 is positioned. The aperture 103 is sized and configured to receive the lead 130 therethrough. A retainer 120 is disposed around the sleeve 104 and is operable to compress or constrict at least a portion of the sleeve 104 against the lead 130 extending through the sleeve. The lead 130 is accordingly retained in position relative to the anchor 100 by friction developed between the sleeve 104 and lead 130 due to the compression force exerted by the retainer 120. In some embodiments, the retainer 120 can extend circumferentially around the sleeve 104 by an amount greater than 180 degrees. In other embodiments, the retainer 120 extends around the sleeve 104 by an amount that is slightly less than 360 degrees (as shown in FIG. 2) or by an amount greater than 360 degrees. In general, the circumferential extent of the retainer 120 is sufficient to capture and/or compress the lead 130 in a generally uniform manner. The sleeve 104 is sized to provide clearance between the inner surface of the aperture 103 and the outer surface of the lead 130 such that the lead 130 may be moved into position relative to the anchor 100 as long as the retainer 120 is maintained in an expanded state (described further below with reference to FIG. 5). The clearance between the sleeve 104 and lead 130 may be, for example and without limitation, in the range of from about 0.001 inch to about 0.002 inch.

In the illustrated embodiment, the retainer 120 has the general form of a circlip (sometimes referred to as a snap ring) with a pair of end portions 124 spaced apart by a gap 122. Each end portion 124 includes an aperture 126 to facilitate actuation with a suitable tool. In this embodiment, the retainer 120 is normally in a contracted state in which the sleeve 104 is compressed against the lead 130. Thus, to insert the lead 130 into the aperture 103, or move the lead 130 within the aperture 103, the retainer 120 is actuated (e.g., elastically deformed) to an expanded state to release the compressive force on the sleeve 104.

Figure 3:
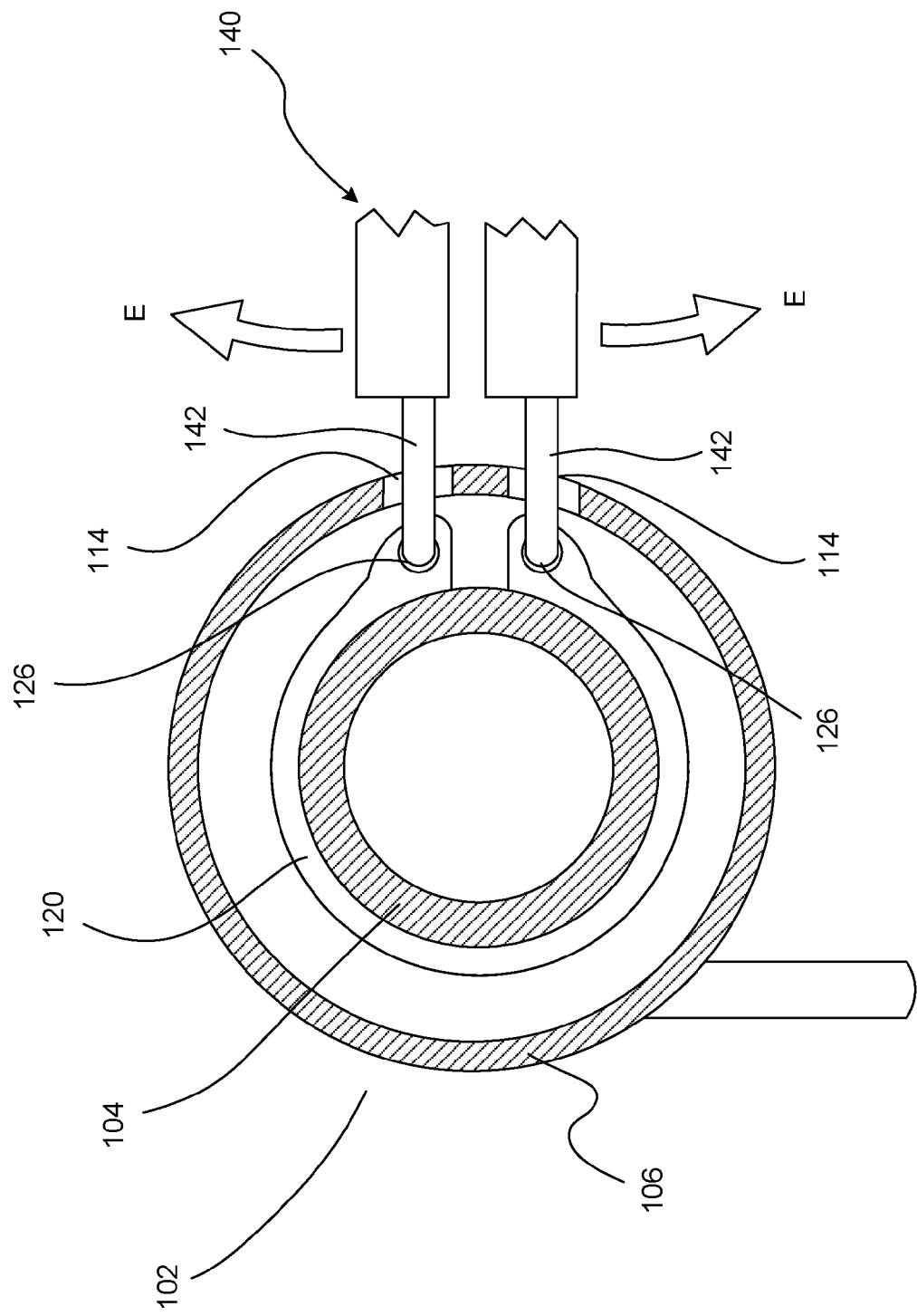
FIG. 3 is a cross sectional view of the lead anchor shown in FIGS. 1 and 2, illustrating a tool engaging the retainer.

FIG. 3 illustrates a representative tool 140 having prongs 142 positioned to expand the retainer 120, as indicated by arrows E. In this embodiment, the retainer 120 is comprised of a material providing a resilient or spring-like behavior. Accordingly, the retainer 120 may be comprised of a metal, such as for example and without limitation, titanium, stainless steel, spring steel, or the like. The retainer 120 may also be formed from resilient plastics, such as, for example and without limitation, ABS, Nylon, Delrin, UHMW polyethylene, and the like.

The anchor body 102 can also include a cover 106 extending around the retainer 120 to prevent or inhibit the retainer from contacting the patient's tissue. The sleeve 104 and cover 106 can be separately manufactured and then assembled together, for example. In this embodiment, the sleeve 104 and cover 106 are formed from a flexible material, such as a biocompatible material. An example of a suitable flexible biocompatible material is silicone rubber. As shown in FIG. 3, the cover 106 includes a pair of openings 114 to allow the tool 140 to be inserted therethrough to engage the apertures 126 of retainer 120. The openings 114 may be in the form of slots (as shown in FIG. 1) extending longitudinally with respect to the anchor body 102. The flexibility of the cover material allows the tool to actuate the retainer 120 without interference from the cover 106. The openings 114 may in other embodiments extend transverse to the anchor body. In still further embodiments, the cover 106 can include a single opening through which the tool 140 is inserted.

It should be appreciated that while certain embodiments disclosed herein are described in the context of a retainer having a normally contracted state, the retainers can have other configurations in other embodiments. For example, in some embodiments the retainer can have a normally expanded state and may be actively contracted to secure the lead 130 in the anchor. Such a retainer may include a latch device (e.g., interlocking teeth) capable of maintaining the retainer in the contracted state. Once the lead 130 is located in the desired position within the anchor, the normally expanded retainer can be compressed (e.g., with a suitable tool) to the contracted state in which the sleeve 104 is compressed against the lead 130. Once the normally expanded retainer is compressed to the contracted state, the latch device maintains the retainer in the contracted state.

Figure 4:
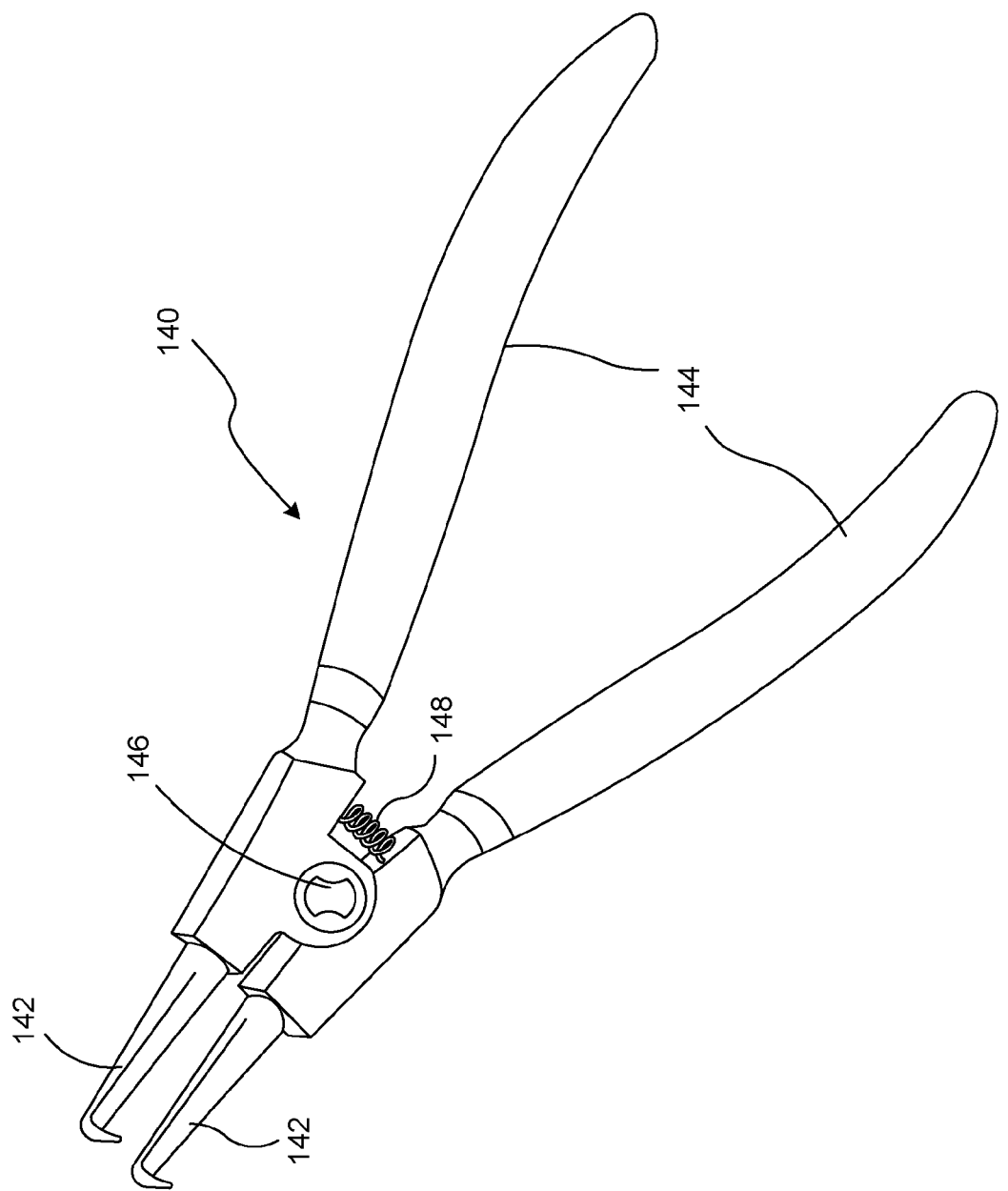
FIG. 4 is a perspective view of representative circlip pliers.

FIG. 4 illustrates a representative embodiment of the tool 140 for actuating the retainer 120 shown in FIG. 3. In this embodiment, the tool 140 is a pair of external circlip or snap ring pliers having 90 degree prongs 142. The pliers 140 include a pair of handles 144 which are pivoted at a pivot joint 146 and maintained in a normally closed position by a spring 148. In this embodiment, the pivot joint 146 is arranged such that when the handles 144 are squeezed (moved toward each other), the prongs 142 move away from each other thereby expanding a contracted circlip. The tool 140 may also be in the form of a hemostat with the tips bent 90 degrees relative to the opening of the hemostat's jaws. In addition, the tool 140 may be locked open or locked closed.

Figure 5:
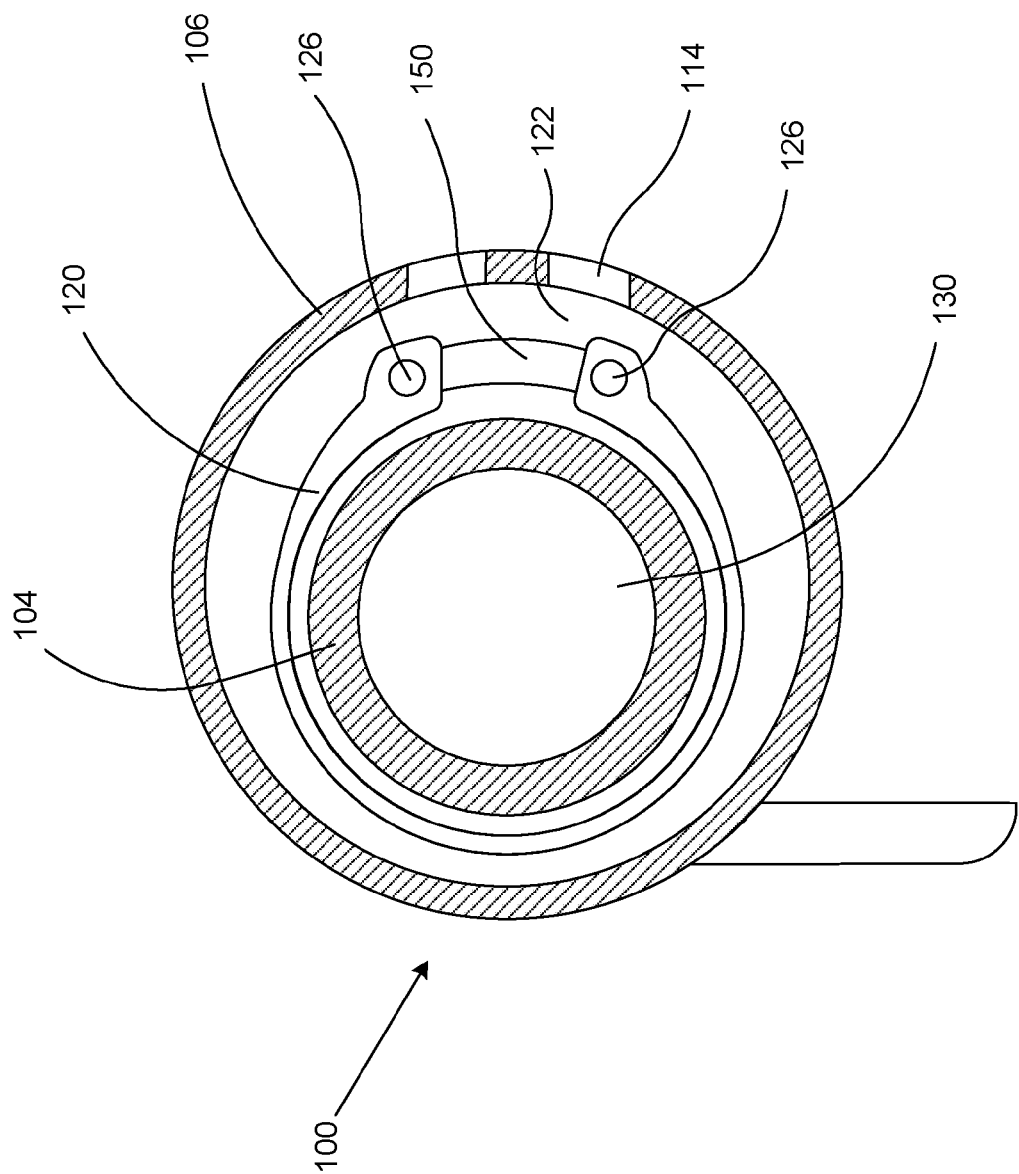
FIG. 5 is a cross sectional view similar to that of FIG. 2 illustrating a spacer installed in the retainer.

FIG. 5 shows the cross section of a lead anchor 100 with the addition of a spacer 150 disposed in the gap 122 between the ends of the retainer 120. Accordingly, the retainer 120 is maintained in an expanded state so that the lead 130 may be inserted into the sleeve 104 without the use of a tool (e.g., the tool 140 described above). Once the lead 130 is positioned within the sleeve 104 at the desired location, a suitable tool is used to compress the retainer 120 thereby sacrificing the spacer 150 and allowing the retainer 120 to contract and compress the sleeve 104 against lead 130. The tool can have a plier arrangement similar to that shown in FIG. 4, but can be configured to compress the circlip to a contracted state when the handles are squeezed together. This type of tool is often referred to as internal circlip or snap ring pliers. In operation, the spacer 150 is broken, deformed or otherwise sacrificed in the process of contracting retainer 120. Accordingly, the spacer 150 may be a frangible material or have a frangible construction. In particular embodiments, the spacer 150 may be a brittle material and easily broken into pieces such that it is out of the way. It should be appreciated that the broken pieces of the spacer 150 are completely encased and captured by the sleeve 104 and/or the cover 106. In other embodiments, the spacer 150 can deform such as by bending. In any of these embodiments, if the lead 130 needs to be repositioned with respect to the anchor 100, a tool may be inserted into slots 114 to engage the retainer apertures 126 as described above in order to temporarily expand the retainer 120 such that the lead 130 may be repositioned.

Figure 6A:
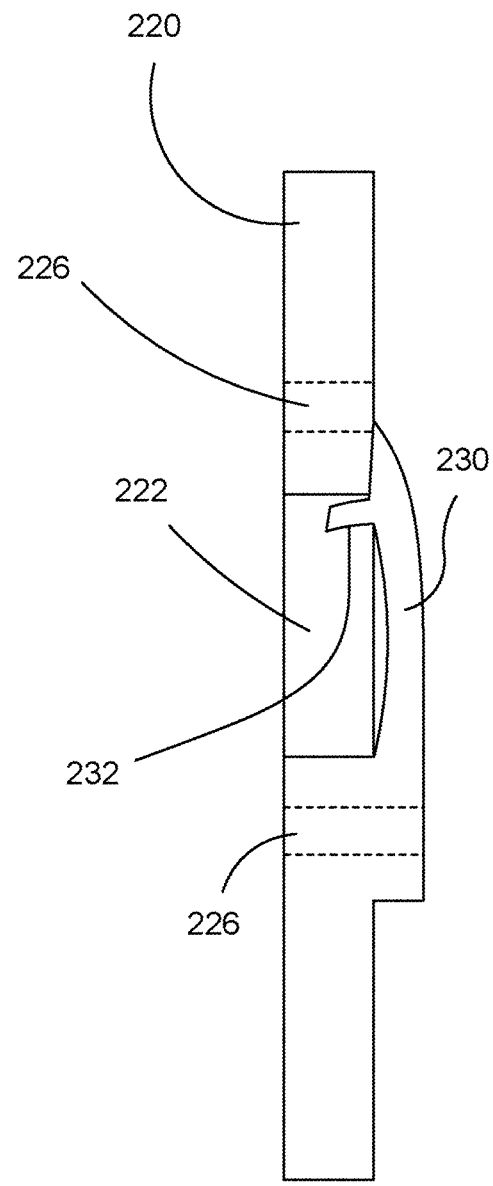
FIG. 6A is a side view from the split end of a retainer illustrating another construction of a spacer.
Figure 6B:
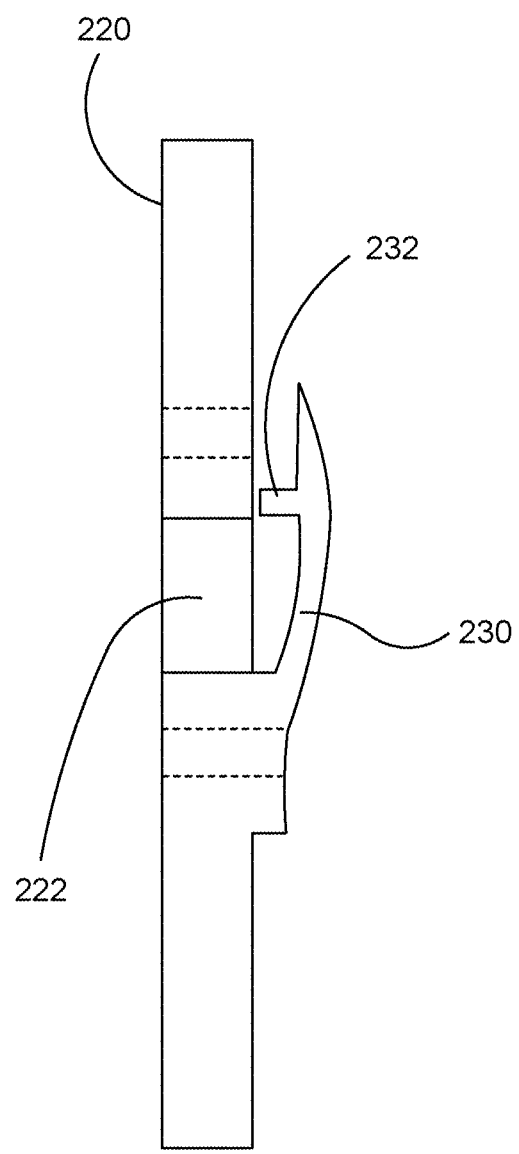
FIG. 6B illustrates the retainer shown in FIG. 6A in a contracted state.

FIGS. 6A and 6B illustrate a retainer 220 configured in accordance with another embodiment of the present technology. FIGS. 6A and 6B are views of the retainer 220 as viewed from a gap 222 between the ends of the retainer. The retainer 220 includes a latch arm 230 which keeps the retainer 220 in an expanded state, as shown in FIG. 6A. The latch arm 230 is carried by one end of the retainer 220 and includes a latch pawl 232 that engages the other end of retainer 220, thereby keeping the retainer 220 in its expanded state. In operation, a user engages the apertures 226 with a suitable tool, such as a pair of internal circlip or snap ring pliers, and urges the ends of the retainer toward each other, thereby contracting the retaining ring 220 while at the same time causing the pawl 232 to disengage from the end of the retaining ring 220, as shown in FIG. 6B. In this case, the retainer 220 is in a normally contracted state except when it is kept in an expanded state by the latch arm 230. Thus, once the pawl 232 is disengaged, the retainer 220 remains contracted in order to squeeze the lead 130 within the associated sleeve 104 (see, e.g., FIG. 5). If the lead 130 is to be repositioned with respect to the anchor 100, a pair of external circlip pliers, such as those shown in FIG. 4, can be used to expand the retainer 220 thereby allowing the pawl 232 to re-engage the end of retainer 220, again maintaining it in an expanded state.

Figure 7:
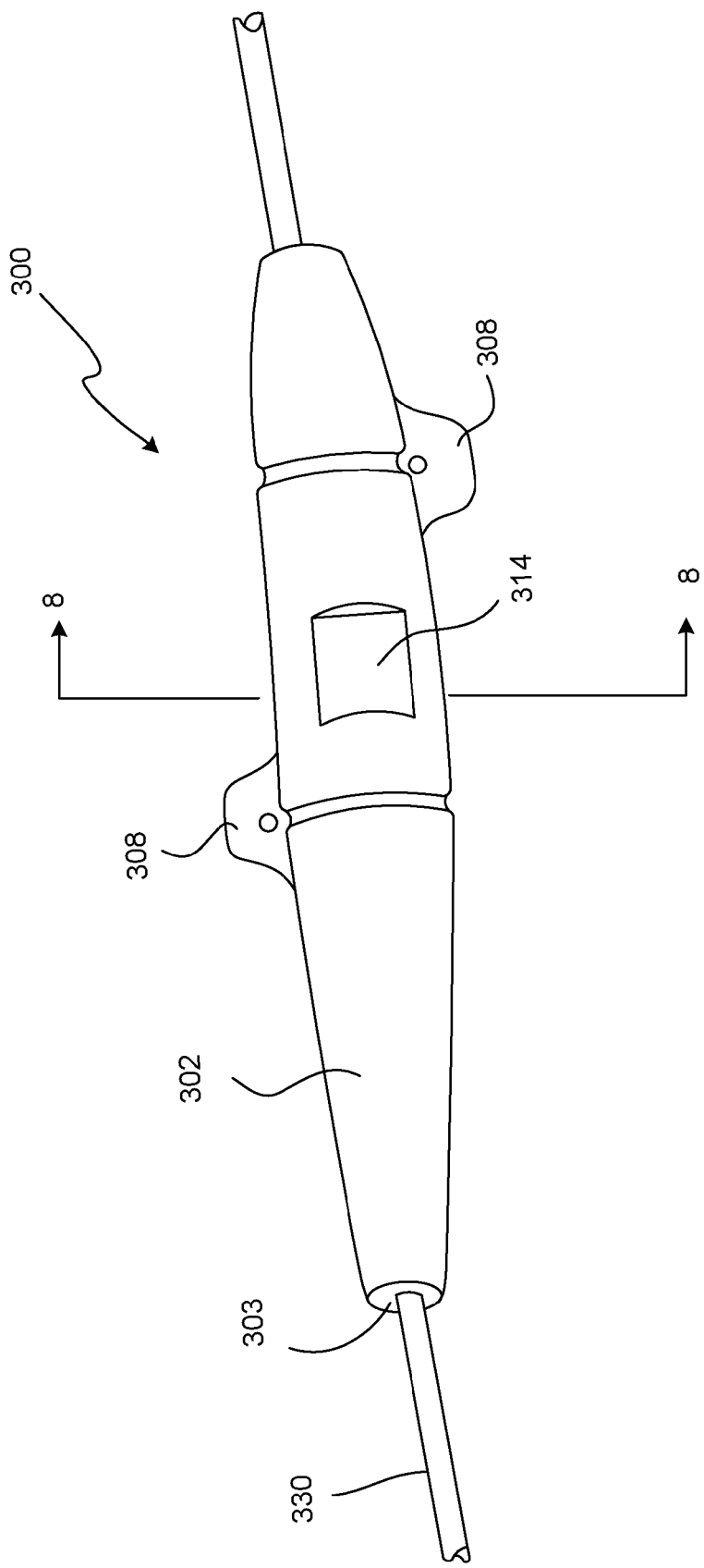
FIG. 7 is a perspective view of a lead anchor according to another representative embodiment.

FIG. 7 illustrates a lead anchor 300 according to another representative embodiment of the present technology. The lead anchor 300 releasably carries a lead 330 and anchors the lead 330 relative to a patient's tissue. Accordingly, the lead anchor 300 can include a longitudinally extending anchor body 302 having a longitudinally extending aperture 303 that receives the lead 330. Similar to the lead anchor 100 described above, one or more anchor tabs 308 can extend laterally from the anchor body 302 to facilitate attaching the lead anchor 300 to a patient. The lead anchor 300 can further include flat sides 314 that allow a user to attach and release the anchor 300 to the lead 330, as described further with reference to FIGS. 8 and 9.

Figure 8:
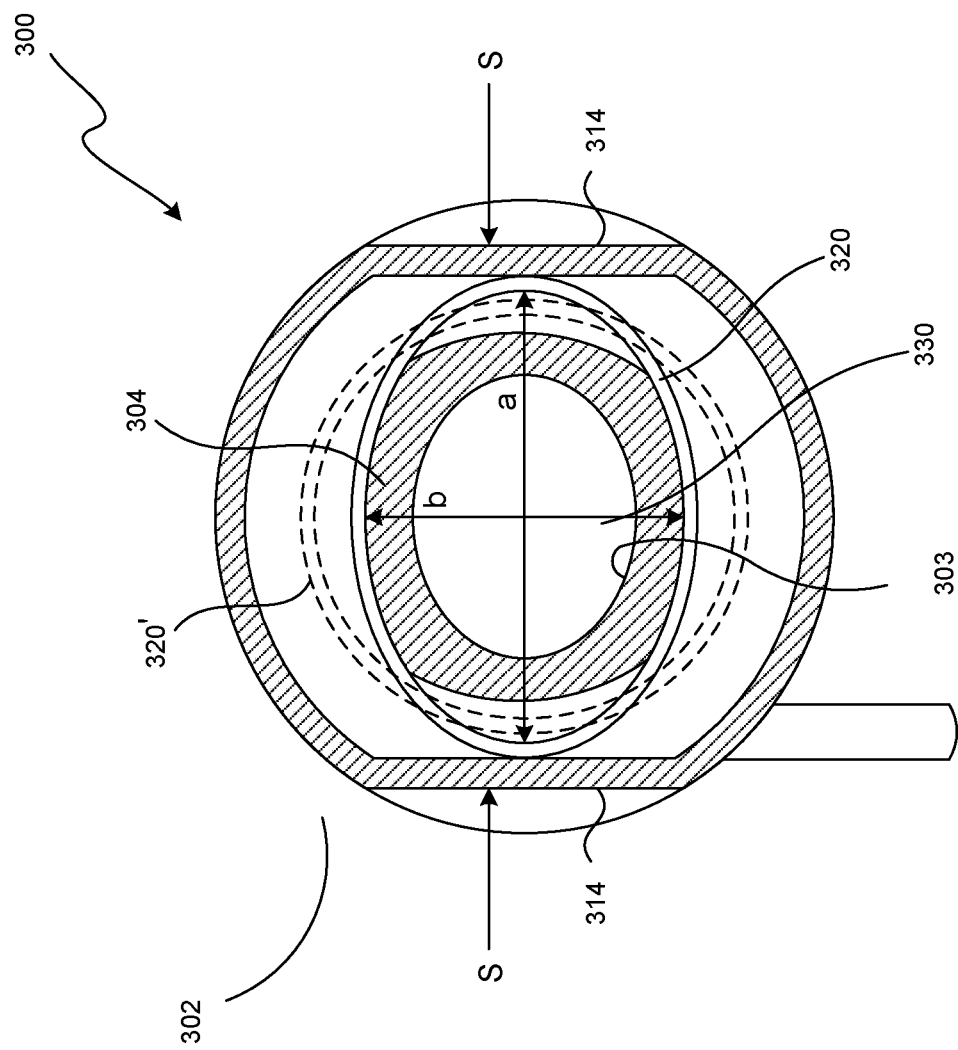
FIG. 8 is a cross sectional view of the lead anchor shown in FIG. 7 taken along line 8-8.

FIG. 8 illustrates a cross-sectional view of the embodiment of the lead anchor 300 shown in FIG. 7. The anchor body 302 includes a sleeve 304 in which the longitudinally extending aperture 303 is positioned. The aperture 303 is sized and configured to receive the lead 330 therethrough. A retainer 320 is disposed around sleeve 304 and is operable to compress or constrict at least a portion of the sleeve 304 against the lead 330 extending through the sleeve. The lead 330 is accordingly retained in position relative to the anchor 300 by friction developed between the sleeve 304 and lead 330 due to the compression force exerted by the retainer 320. The sleeve 304 is sized to provide clearance between the inner surface of the aperture 303 and the outer surface of the lead 330 such that the lead 330 may be moved into position relative to the anchor 300 as long as the retainer 320 is maintained in an expanded state indicated in dashed lines in FIG. 8 by reference number 320'.

Figure 9:
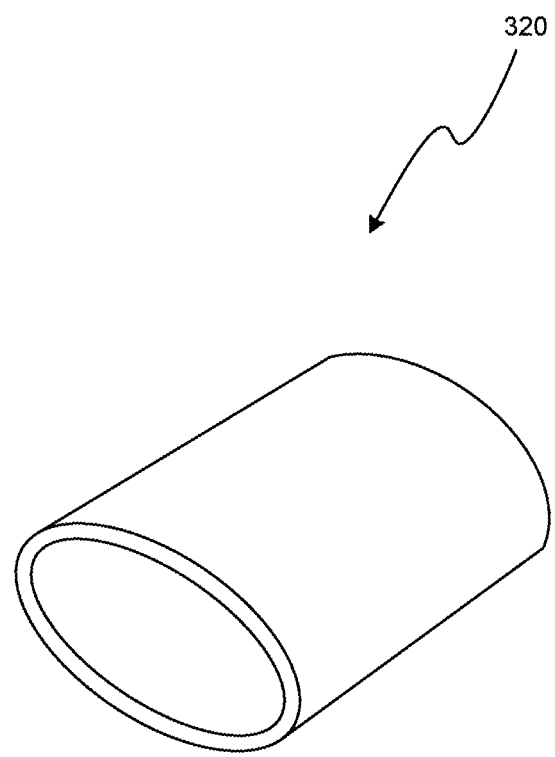
FIG. 9 is a perspective view of a tubular retainer as shown in FIG. 8.

As illustrated in FIGS. 8 and 9, the retainer 320 has the general form of an elongate tube having an oval or elliptical cross-section. In this embodiment, the retainer 320 is normally in a contracted state (e.g., with an elliptical cross-section) in which the sleeve 304 is compressed against the lead 330 across the minor axis b of the retainer 320. Thus, to insert the lead 330 into the aperture 303, or move the lead 330 within the aperture 303, the retainer 320 is actuated (e.g., elastically deformed) to an expanded state as indicated in dashed lines by reference number 320' (e.g., to a circular cross-sectional shape) to release the compressive force on the sleeve 304.

The retainer 320 is actuated by squeezing the major axis a of the retainer 320 with a suitable tool, such as a hemostat, as indicated by arrows S. Squeezing the major axis a of the retainer 320 causes the cross-section of the retainer 320 to deform and move toward a more circular shape as indicated by reference number 320'. The flat sides 314 are formed in the anchor body 302 at the location of the retainer's major axis a in order to indicate where to squeeze the anchor body 302 to actuate the retainer 320. In other embodiments, the anchor body 302 can include grooves or color markings to indicated the proper location to squeeze the anchor body 302 to actuate the retainer 320.

In another embodiment, the retainer can include a material (e.g., nickel-titanium alloy) that has a circular cross-section at room temperature but changes to an oval or elliptical cross-section at a temperature between room temperature and body temperature (e.g., 98.6° F.). Accordingly, the lead anchor can be freely repositioned with respect to the lead prior to implanting the lead into a patient. Once the lead and lead anchor are implanted, the patient's body temperature causes the retainer to move to a contracted state, thereby retaining the lead in position with respect to the lead anchor. The lead anchor can be repositioned while implanted in the patient's body by actuating the retainer as explained above with respect to FIGS. 8 and 9.

The present technology also includes methods of anchoring a lead to a patient using a lead anchor. A representative method comprises inserting a lead into a sleeve; maintaining a retainer disposed around the sleeve in an expanded state; manually moving the retainer to a contracted state; and maintaining the retainer in the contracted state around the sleeve, thereby squeezing the sleeve against the lead. The method can further comprise moving the retainer to the expanded state and repositioning the lead with respect to the sleeve. The method can still further comprise attaching the sleeve to a patient with sutures.

Several embodiments described herein offer advantages over traditional lead anchors. For example, certain embodiments include a retainer that retains the lead in position with fewer parts than traditional lead anchors have. Accordingly, the disclosed lead anchors can be smaller than traditional lead anchors which results in a device that is more comfortable for the patient. With fewer parts, the lead anchor can be more economical to produce when compared to traditional lead anchors having additional parts. The disclosed lead anchors are also easy to use. With one movement of a suitable tool, the retainer may be contracted or expanded in order to position, reposition, or secure a lead within the lead anchor sleeve. Certain embodiments of the lead anchor include a cover. The cover provides an advantage over traditional lead anchors in that the cover encloses the retainer and protects the patient's tissue from contacting the retainer. Other lead anchors have exposed components that can irritate tissue.

The present technology includes lead anchors for use with neurological stimulation systems, such as spinal cord modulation systems. In a representative embodiment, the lead anchor comprises a longitudinally extending sleeve having an aperture sized and positioned to receive a lead. A retainer is disposed around the sleeve and is operative to compress at least a portion of the sleeve against a portion of the lead that extends through the sleeve. The lead anchor may further comprise a cover extending around the retainer.

In another representative embodiment, a spinal cord lead anchor comprises a longitudinally extending sleeve having an aperture sized and positioned to receive a spinal cord lead. A retainer is disposed around the sleeve and is operative to compress at least a portion of the sleeve against a spinal cord lead extending through the aperture. A cover extends over the retainer and includes at least one opening formed through the cover to facilitate engaging the retainer with a tool. The lead anchor also includes a pair of anchor tabs to facilitate attaching the lead anchor to a patient.

In one aspect of the technology disclosed herein, the cover can include a pair of longitudinally extending slots, to facilitate engaging the retainer with a tool. In another aspect of the disclosed technology, the retainer is a circlip having a pair of apertures engageable with a tool. In yet another aspect of the disclosed technology, the anchor can further comprise a spacer disposed between ends of the circlip and operative to maintain the circlip in an expanded state until the spacer is compressed. The spacer can be, for example, frangible or deformable.

In further aspects of the disclosed technology, the anchor tabs extend from the cover and each includes an anchor aperture. The cover can also include two grooves, each aligned with one of the anchor tabs. In some embodiments, the retainer is a normally contracted circlip having a pair of apertures engageable with a tool. In other embodiments, the retainer is normally expanded and includes a latch device capable of maintaining the retainer in a contracted state.

In a further representative embodiment, a method of anchoring a lead comprises inserting a lead into a sleeve while a retainer disposed around the sleeve is in an expanded state; contracting the retainer to a contracted state; and compressing the sleeve against the lead with the retainer while the retainer is in the contracted state. The method can further comprise placing the retainer in the expanded state and repositioning the lead with respect to the sleeve. The method can further comprise attaching the sleeve to a patient.

From the foregoing, it will be appreciated that specific embodiments of the disclosed technology have been described herein for purposes of illustration, but that various modifications may be made without deviating from the technology. For example, in a particular embodiment the cover may be provided with a single opening to provide access to the retainer. In some embodiments, the opening may extend transverse to the longitudinally extending sleeve. In other embodiments, the opening comprises a slit formed in the flexible material of the cover. In still other embodiments, the ends of the retainer can include other features besides apertures that a suitable tool can engage in order to actuate the retainer. For example, the ends of the retainer can include flats or hook features. In certain embodiments, the anchor tabs can extend from one side or both sides. In yet further particular embodiments, representative anchors in accordance with the present technology can be used to secure medical devices other than neural stimulation leads. Representative stimulation systems and associated therapies are disclosed in the following references, all of which are incorporated herein by reference: U.S. application Ser. Nos. 12/264,836; 13/607,617; and U.S. Pat. No. 8,712,533. To the extent that the foregoing references and/or any other material incorporated herein by reference conflict with the present disclosure, the present disclosure controls.

Certain aspects of the disclosure described in the context of particular embodiments may be combined or eliminated in other embodiments. For example, in some embodiments the anchor tabs can be eliminated. In other embodiments, the grooves associated with the anchor tabs can be eliminated. In certain embodiments in which the retainer is formed from a biocompatible material, the cover can be eliminated. Any of the elements of the technology disclosed herein can be combined in any suitable combination. For example, the retainer 220 described with respect to FIGS. 6A and 6B can be combined with the lead anchor 100.

Further, while advantages associated with certain embodiments have been described in the context of those embodiments, other embodiments may also exhibit such advantages, and not all embodiments need necessarily exhibit such advantages to fall within the scope of the present disclosure. Accordingly, the present disclosure and associated technology can encompass other embodiments not expressly shown or described herein.

I claim:

1. A lead anchor, comprising:
a longitudinally extending sleeve having an aperture sized and positioned to receive a lead therethrough;
a retainer disposed around the sleeve and operative to compress at least a portion of the sleeve against a lead extending through the aperture;
a cover extending around the retainer; and
a spacer positioned to maintain the retainer in an expanded state.

2. The lead anchor of claim 1, wherein the cover includes at least one opening aligned with the retainer to provide access to the retainer from outside the cover.

3. The lead anchor of claim 2, wherein the retainer is a circlip having a pair of apertures engageable with a tool.

4. The lead anchor of claim 3, wherein the openings comprise a pair of longitudinally extending slots aligned with the pair of apertures.

5. The lead anchor of claim 1, wherein the spacer is frangible.

6. The lead anchor of claim 1, wherein the spacer is deformable.

* * * * *